United States Patent
Shinohara

[11] Patent Number: 5,824,742
[45] Date of Patent: Oct. 20, 1998

[54] POLYACETAL RESIN COMPOSITION AND MOLDED ARTICLE THEREOF

[75] Inventor: Kenichi Shinohara, Yokohama, Japan

[73] Assignee: E. I. du Pont de Nemours and Company, Wilmington, Del.

[21] Appl. No.: 913,265

[22] PCT Filed: Mar. 13, 1996

[86] PCT No.: PCT/US96/03429

§ 371 Date: Sep. 10, 1997

§ 102(e) Date: Sep. 10, 1997

[87] PCT Pub. No.: WO96/28510

PCT Pub. Date: Sep. 19, 1996

[30] Foreign Application Priority Data

Mar. 13, 1995 [JP] Japan ........................................ 7-52347

[51] Int. Cl.$^6$ ...................................................... C08L 53/00
[52] U.S. Cl. ............................ 525/88; 525/100; 525/185; 525/471; 525/472; 525/474; 525/521; 525/540
[58] Field of Search ............................. 525/88, 100, 185, 525/471, 472, 474, 521, 540

[56] References Cited

FOREIGN PATENT DOCUMENTS

| 0290230 A3 | 11/1988 | European Pat. Off. . |
| 0420564 A3 | 4/1991 | European Pat. Off. . |
| 04234450A | 8/1992 | Japan . |
| WO 93/11206 | 6/1993 | WIPO . |

OTHER PUBLICATIONS

Interantional Search Report Jul. 11, 1996.

*Primary Examiner*—Samuel A. Acquah

[57] ABSTRACT

An objective of the invention is to provide a polyacetal resin composition which has excellent resistance to heat aging and grease resistance, has welded sections with no decrease in physical properties, and has improved friction characteristics, and molded articles therefrom. A polyacetal resin composition comprising per 100 parts by weight of a polyacetal resin, 2–7 parts by weight of a polymer composition based on an olefinic polymer having glycidyl-group-containing pendant chains and 0.5–2.5 parts by weight of a dimethyl siloxane polymer of a plasticity of at least one; a polyacetal resin composition further comprising 100 parts by weight of the preceding resin composition along with 0.05–0.5 parts by weight of carbon black; and molded articles therefrom.

6 Claims, 1 Drawing Sheet

POLYACETAL RESIN COMPOSITION AND MOLDED ARTICLE THEREOF

FIELD OF THE INVENTION

The present invention relates to a polyacetal resin composition, specifically to a resin composition materially comprising a polyacetal resin, a polymer composition based on an olefinic polymer having glycidyl-group-containing pendent chains and a dimethyl siloxane polymer; and this resin composition containing, in addition, carbon black. The invention also relates to a molded article, obtained by molding these resin compositions, having excellent resistance to heat aging and grease resistance, and no loss in physical properties in molded sections, along with improved abrasion resistance characteristics.

DESCRIPTION OF THE RELATED ART

Polyacetal resins, which are plastic materials with excellent repeated fatigue characteristics and wear resistance and well balanced mechanical properties, are used in a broad area, such as in automobiles and electrical and electronic parts, and the like. However, polyacetal resin, in general, tends to oxidatively degrade at high temperatures with mechanical properties decreasing too rapidly to be maintained when subjected to repeated usage at the high temperatures of 90°–120° C.

Many proposals have been made for improving resistance to heat aging (long term heat stability) which, for example, includes methods of adding antioxidants and heat stabilizers, such as polyamides and polydicarboimide as disclosed in U.S. Pat. Nos. 4,098,843 and 4,845,161. Japanese Patent Laid Open H4-345649 discloses a polyacetal resin composition with improved resistance to heat aging and grease resistance (long term oil resistance) comprising a polyacetal resin and a compound having epoxy, nitrile groups and/or oxazolyl groups as functional groups.

The present inventors developed and proposed (Japanese Patent Application Publication H6-111711), an improved polyacetal resin composition which has resistance to heat aging and grease resistance and has welded sections with no decrease in physical properties, which materially comprises a polyacetal resin, an olefinic type polymer having glycidyl-group-containing pendent chains, and a styrene polymer having an oxazolyl-group-containing pendent chains.

Problems to be Solved by the Invention

Much improvement has been made on polyacetal resins as described above. Molded articles using these improved polyacetal resin compositions, such as molded gears, switches, rollers, switch mechanism parts, cams, and the like, which are subjected to high loads, sometimes in their service suffer from problems of wear or squeaking problems, for which further improvement has been required on wear resistance, or the like, friction characteristics.

It is an objective of this invention to provide a polyacetal resin composition which has excellent resistance to heat aging and grease resistance and has welded sections with no decrease in physical properties, along with further improved friction characteristics of the polyacetal resin.

SUMMARY OF THE INVENTION

This invention relates to a polyacetal resin composition having per 100 parts by weight of a polyacetal resin, 2–7 parts by weight of a polymer composition based on an olefinic polymer having glycidyl-group-containing pendant chains and 0.5–2.5 parts by weight of a dimethyl siloxane polymer of a plasticity of at least one, as well as molding articles made from the resin composition.

DETAILED DESCRIPTION

Figure 1:
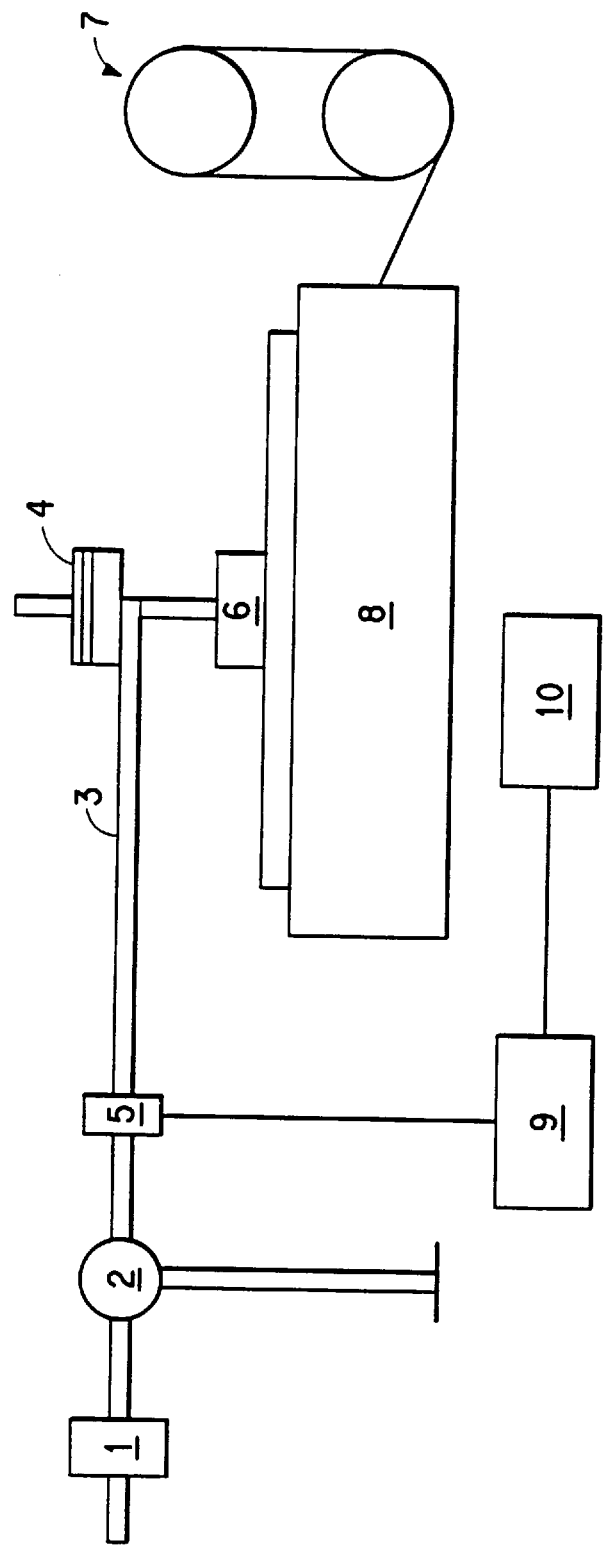
FIG. 1 is a schematic diagram for the reciprocating friction wear tester used in the friction characteristic evaluation test.

The means for solving the problems in the prior art are as follows.

The present inventors discovered that the addition of a dimethyl siloxane polymer to a polyacetal resin composition materially comprising a polyacetal resin, an olefin type polymer having glycidyl containing pendent chains, and a styrene polymer having oxazolyl-group-containing pendent chains, considerably improves wear resistance, and that an additional incorporation of carbon black substantially decreases the wear rate.

The present invention is a polyester resin composition comprising per 100 parts by weight of a polyacetal resin, 2–7 parts by weight of a polymer composition based on an olefinic polymer having glycidyl-group-containing pendent chains and 0.5–2.5 parts by weight of a dimethyl siloxane polymer of a plasticity of at least one, as well as molded articles therefrom.

Specifically, the present invention is a resin composition in which, in the above composition, (a) the polymer composition is a resin composition of a single olefinic polymer having glycidyl-group-containing pendent chains;

(b) the polymer composition is a melt blend of 100 parts by weight of an olefinic polymer having glycidyl-group-containing pendent chains and 50–200 parts by weight of a styrene polymer having an oxazolyl group.

(c) a resin composition obtained by adding 0.05–5 parts by weight of carbon black per 100 parts by weight of the above resin compositions (a) and (b);

and molded articles of each of the preceding resin compositions (a), (b), and (c).

The resin compositions of this invention may use common polyacetal resins as the polyacetal resin component, such as homopolymers or their copolymers of an aldehyde, such as formaldehyde, a cyclic oligomer of formaldehyde, such as trioxane, tetraoxane, or the like, or copolymers of these aldehydes with cyclic ethers or acetals, such as ethylene oxide, propylene oxide, 1,3-dioxolane, or the like.

These polyacetal resins mainly are polymers having main chains of repeating units represented by —(CH$_2$O)n— (n represents a positive number) and/or —(CHR—O)n— (where R is an alkyl group; n is a positive number) having terminii which are not protected or are protected with protecting groups such as —OCH$_3$, —OCF$_3$, —OCH$_2$OH, having number average molecular weights of 10,000–100,000, preferably 20,000–70,000.

A melt blend is used as a polymer composition based on an olefinic polymer having glycidyl-group-containing pendent chains in the resin composition of this invention which is either an olefin polymer having glycidyl-group-containing pendent chains or a melt blend of this olefinic polymer and a styrene polymer having an oxazolyl group.

Olefinic polymers having glycidyl-group-containing pendent chains include, for example, random ethylene/glycidyl (meth)acrylate copolymers, random ethylene-methyl(meta)

acryl-glycidyl(meth)acrylate terpolymers, random ethylene-butyl(meth)acrylate-glycidyl(meth)acrylate terpolymers, random ethylene-vinylacetate-glycidyl(meth)acrylate terpolymers, and the like, either singly or in a mixture of two or more, without being limited to these examples.

Silane polymers having oxazolyl groups are, for example, copolymers of 2-vinyl-oxazoline and styrene, which can be readily manufactured via a well known radical copolymerization reaction.

Incorporating a polymer composition into the polyacetal resin improves the resistance to heat aging and grease resistance of its molded articles, but use of a melt blend, particularly of an olefinic polymer having glycidyl-group-containing pendent chains and a styrene polymer containing an oxazolyl group, further improves resistance to heat aging than is possible with single use of an olefinic polymer having glycidyl-group-containing pendent chains. Too small an amount of the polymer composition incorporated will fail to give a sufficient improvement effect on resistance to high temperature heat aging and grease resistance, while too large an amount will adversely affect the high strength and high modulus, which are the inherent mechanical properties of the polyacetal resin molded article. The preferred amount compounded is 2–7 parts by weight per 100 parts by weight of the polyacetal resin.

If the polymer composition used is a melt blend of an olefinic polymer having glycidyl-group-containing pendent chains and a styrene polymer with oxazolyl groups, use is made of a melt blend comprising 100 parts by weight of an olefinic polymer having glycidyl-group-containing pendent chains and 50–200 parts by weight of a styrene polymer having an oxazolyl group. If the amount of the styrene polymer having oxazoylyl groups is too small, olefinic polymer particles having glycidyl-group-containing pendent chains can no longer be incorporated into the styrene polymer having an oxazolyl group, and instead will be present by themselves in the polyacetal resin, which will not only decrease considerably the welding strength of the molded article, but also will cause crack formation due to nonuniform dispersion. On the other hand, if the amount of styrene polymer having an oxazolyl group in in too high an amount, there will be no synergistic operation of the the heat stabilizing effect by a styrene polymer having an oxazolyl group and a heat stabilizing effect by an olefinic polymer having a glycidyl group, thus failing to improve sufficiently the heat aging resistance.

The resin composition of this invention uses a dimethyl siloxane polymer which has a plasticity as measured by a Williams' Plastometer of 1.0 or higher, preferably 1.4–1.9. Too low a plasticity means that the composition during the melt kneading of the resin composition or during molding will show a phenomenon of slipping on the screw surface in a kneader or molding machine, which makes it difficult to fill a specific amount into the mold. These dimethyl siloxane polymers, in general, have extremely high polymer viscosities, for which it is difficult to express as the viscosity of a conventional silicone oil, being a polymer having a far higher viscosity than the viscosity of 150,000 cs of the silicone polymers which are conventionally used as lubricants. The average DPC molecular weights are about 550,000 to 700,000.

The dimethyl siloxne polymer improves the wear resistance of the molded articles, but if the amount compounded is too small, no satisfactory improvement is obtained on the wear resistance of the molded articles; while if the amount is too high, it not only adversely affects the moldability, but it also decreases the wear resistance of the molded articles.

The suitable amount of the dimethyl siloxane polymer to be incorporated is 0.5–2.5 parts by weight per 100 parts by weight of the polyacetal resin.

Incorporating carbon black into the above resin composition of this invention gives a resin composition with further improved moldability and wear resistance of the molded article. A suitable amount of carbon black incorporated is 0.05–0.5 parts by weight per 100 parts by weight of each resin composition. If the amount of the carbon black compound is too small, there is no significant effect on improving the the wear resistance of the molded article; while if it is too high an amount, this not only causes an adverse affect on moldability due to nonuniform dispersion or thermal degradation, but it also decreases the mechanical properties of the molded articles, particularly their impact resistance, along with a reduction in their wear resistance.

Each resin composition of this invention, within the range of not adversely affecting its inherent properties, may be mixed with a variety of additives which are normally added to the polyacetal resin, for example, an antioxidant, a heat stabilizer, a formaldehyde trap, a UV absorber, a coloring pigment, a mold release, a lubricant, or the like.

A resin composition based on a polyacetal resin of this invention can be readily prepared by a known method, for example, by mixing well each of these components followed by melt kneading using a single screw or twin screw extruder, or the like, thereby preparing pellets.

If a melt blend is used as the polymer composition comprising an olefinic polymer having glycidyl-group-containing pendent chains and a styrene polymer having an oxazolyl group, it is preferred to prepare pellets by a method similar to the above from a melt blend of an olefinic polymer having glycidyl-group-containing pendent chains and a styrene polymer having an oxazolyl group followed by melt-kneading again the resultant pellets with other components. Use of this method allows the styrene polymer having an oxazolyl group to incorporate the olefin polymer having glycidyl pendent chains, forming a core-shell structure with a high probability.

The various resin pellets of this invention may be used to prepare, by molding by the usual methods, molded articles that have resistance to heat aging and grease resistance, and that have welding sections with minimal decrease in physical properties and excellent wear resistance.

EXAMPLES (1) Preparation of Resin Compositions a) Components Used for Polyacetal Resin Polyacetal homopolymer standard resin (tradename Delrin 500 PNC 10, manufactured by the Dupont Company).

Polymer Composition:

A: Random ethylene-glycidyl methacrylate-N-butylacrylate terpolymer (monomer content: 5% glycidyl methacrylate and 30% N-butylacrylate, manufactured by the DuPont Company).

B: A polymethyl methacrylate (PMM) grafted copolymer of an ethylene/glycidyl methacrylate copolymer (EGMA) (monomer content: glycidyl methacrylate 10.5%, EGMA/PMMA=70/30; tradename: Modibar [Phonetic Translation] 4200, manufactured by Nippon Yushi K.K.).

C: A random copolymer of 2-vinyl oxazoline (monomer content: 5%) and styrene (tradename: Epicross RPS-005, manufactured by Nippon Shokubai K.K.).

D: Pellets obtained by mixing 60 parts of polymer composition A and 40 parts by weight of C, followed by melt kneading at barrel a temperature of 190° C. using a conventional extruder, followed by water cooling and cutting.

Silicone Gum Concentrate: Polyacetal resin (tradename: Delrin DE8100 HBNC100, manufactured by the DuPont Company) was fed to a twin screw extruder, melt kneaded at a resin temperature of 190°–21° C., followed by adding at the rate of 40 parts by weight, with respect to 100 parts by weight of polyacetal resin of a dimethyl siloxane polymer (DMSP) (BY16-140, manufactured by Toray Silicone K.K.) at a high degree of polymerization having a plasticity of 1.40–1.90 which has been softened at a high temperature, through a side feeder, followed by cooling and cutting, thereby generating a polyacetal resin-based silicon gum concentrate.

Carbon Black:

BK-1: Carbon 35 (manufactured by Mitsubishi Kasei K.K.)

BK-2: Vulcan 9 (manufactured by Cabot K.K.)

b) Preparation of Resin Composition 10 kg of a polyacetal resin was melt kneaded with a polymer composition, a silicone gum concentrate and/or with or without carbon black, using a 35 mm twin screw extruder (DEM 35, manufactured by Toshiba K.K.), followed by water cooling and cutting to prepare resin compositions of this invention (samples 1–9) and comparative resin compositions (samples 11–19).

The composition of each pellet prepared is given in Table 1.

(2) Preparation of Molded Articles (Test Pieces) and Evaluation of Moldability

Each pelletized product prepared in the above was injection molded out of the usual conditions to prepare test pieces for various tests.

Moldability was evaluated under the following basis in the molding of these test pieces by observing the surface appearance around the gate, with the rating results given in Table 1:

⊚: Excellent

○: Surface wrinkles were observed only in the vicinity around the gate.

Δ: Surface wrinkles were observed on a broader range around the gate.

X: Surface peels were observed.

(3) Friction Characteristics Evaluation Test a) Reciproacting Friction Wear Tester The friction characteristics evaluation test was carried out using the reciprocating friction wear tester (developed by our company) illustrated in FIG. 1. In FIG. 1, the numbers on the drawing represent the following components:

1—Balance Regulator

2—Pressure Sensor

3—Arm

4—Load (M)

5—Test Piece on the Reciprocating Table Side

6—Test Piece on the Arm Side

7—Motor

8—Reciprocating Table A

9—Computer

10—Recorder

The reciprocating friction wear tester, as illustrated by FIG. 1, is a Table (A) which reciprocates back and forth and an arm (B) which can be balanced by a weight. The reciprocating Table (A) on which a test piece is fixed is caused to reciprocate back and forth at a specific periodicity by a rotating disk connected to it. A triangular-shaped flat test piece is secured on one end of the arm (B), on which a weight can be placed to adjust the load (M). As the reciprocating Table (A) starts its reciprocating motion and a test piece fixed on arm (B) slides over the test piece fixed on reciprocating Table (A), a pressure sensor incorporated into the other end of arm (B) measures a frictional torque (Y) acting on the reciprocating motion which is then recorded on a recorder. This permits varying the load (M) to measure the change (YI) in frictional torque.

b) Coefficient of Dynamic Friction (u)

The reciprocating friction wear tester illustrated in FIG. 1, explained by the above, was used to calculate the coefficient of dynamic friction (u) of each test piece according to Equation 1 which is then given in Table 1.

| Load($M_1$–$M_s$) | 0.5, 1.0, 1.5, 2.0, 3.0 kg |
|---|---|
| Reciprocating Length | 6.5 cm |
| Rotation Speed (Periodic Speed) | 4 rpm |
| Test Pieces: | |
| The Arm Side | Triangular Flat Sheet 6.4 mm thick |
| Reciprocating Table Side | 3.2 mm-t × 18 mm × 100 mm |

Equation 1

Coefficient of Dynamic Friction (u)=

$$(0.5\ y_1 + 1.0\ y_2 + \ldots + 3.0\ y_5)^2 / (0.5^2 + 1.0^2 + \ldots + 3.0^2)$$

c) WearRate (W)

The reciprocating friction wear tester was used in a manner similar to the above to calculate the difference in the test piece weight before test ($W_0$) and test piece ($W_1$) measured after testing under the following conditions, thereby resulting in a wear rate (W) (mg) which is given in Table 1:

| Load (M) | 3.0 kg |
|---|---|
| Reciprocating Length | 7.5 cm |
| Rotary Speed (Periodical Speed) | 60 rpm |
| Number of Reciprocations | 10,000 cycles |
| Test Pieces: | |
| Arm Side: | Triangular Flat Sheet 6.4 mm thick |
| Reciprocating Table Side | 3.2 mmt × 18 mm × 100 mm |

(4) Heat Degradation Test (Resistance to Heat Aging and Grease Resistance)

A test piece was coated with a lithium based grease (tradename: Marutenptar 2 [Phonetic Translation], manufactured by Kydo Yushi K.K.) followed by holding for 188 hours in a 135° C. oven and then carrying out the tensile test, thereby calculating percent retention with respect to the initial strength of each sample.

The resistance to heat aging and grease resistance were rated according to the following basis from the computer results of percent retention and were reported as grease resistance in Table 1.

○: % retention—80% or greater

X; % retention—less than 80%.

TABLE 1

|  | Samples Nos. | | | | | | | | |
|---|---|---|---|---|---|---|---|---|---|
| Examples | 1 | 2 | 3 | 4 | 5 | 6 | 7 | 8 | 9 |
| Resin Composition (parts by wt.) | | | | | | | | | |
| Polyacetal resin | 100 | 100 | 100 | 100 | 100 | 100 | 100 | 100 | 100 |
| Polymer composition | | | | | | | | | |
| Type | A | A | A | B | D | A | A | A | B |
| Amount compounded | 5.0 | 3.0 | 5.0 | 5.0 | 5.0 | 5.0 | 5.0 | 3.0 | 3.0 |
| DMSP | 1.0 | 1.0 | 2.0 | 2.0 | 1.0 | 1.0 | 1.0 | 2.0 | 1.0 |
| Carbon Black | — | — | — | — | — | BK1 | BK2 | BK2 | BK2 |
| Friction Characteristics | | | | | | | | | |
| Coefficient of Friction ($\mu$) | 0.07 | 0.08 | 0.05 | 0.06 | 0.06 | 0.07 | 0.07 | 0.05 | 0.07 |
| Wear Rate ($\Delta$ W:mg) | 1.2 | 2.6 | 6.5 | 7.8 | 6.3 | 0.4 | 0.5 | 3.0 | 2.0 |
| Moldability | ○ | ⊚ | ○ | ○ | ⊚ | ⊚ | ⊚ | ⊚ | ⊚ |
| Grease Resistance | ○ | ○ | ○ | ○ | ○ | ○ | ○ | ○ | ○ |
| Comparative Examples | 11 | 12 | 13 | 14 | 15 | 16 | 17 | 18 | 19 |
| Resin Composition (parts by wt.) | | | | | | | | | |
| Polyacetal resin | 100 | 100 | 100 | 100 | 100 | 100 | 100 | 100 | 100 |
| Polymer composition | | | | | | | | | |
| Type | — | — | A | A | A | A | C | — | C |
| Amount compounded | — | — | 5.0 | 1.0 | 5.0 | 10.0 | 5.0 | — | 5.0 |
| DMSP | — | 2.0 | — | 1.0 | 3.0 | 1.0 | 1.0 | — | 2.0 |
| Carbon Black | — | — | — | — | — | — | — | BK1 | BK2 |
| Friction Characteristics | | | | | | | | | |
| Coefficient of Friction ($\mu$) | 0.39 | 0.04 | 0.22 | 0.08 | 0.03 | 0.15 | 0.08 | 0.34 | 0.05 |
| Wear Rate ($\Delta$ W:mg) | 85.0 | 0.8 | 16.5 | 18.0 | 23.5 | 18.5 | 20.5 | 42.4 | 21.8 |
| Moldability | ⊚ | X | Δ | ○ | X | X | ○ | ⊚ | Δ |
| Grease Resistance | X | X | ○ | X | X | X | ○ | X | ○ |

The amount of DMSP (dimethyl siloxane polymer) was calculated from the amount of a silicone concentrate added. The amounts of carbon black added all were 0.3 parts by weight.

All of the samples of the examples containing both the polymer composition and dimethyl siloxane polymer within the defined ranges show good moldability, as well as excellent friction characteristics; in particular, each sample containing carbon black show further improved moldability and wear rate. On the other hand, the control examples which either contain none of the polymer compositions and dimethyl siloxane polymer or which may contain outside of the designated ranges, each fail to strike a balance in moldability and friction characteristics.

Samples containing a dimethyl siloxane polymer within the designated range each maintain the resistance to heat aging and grease resistance which are inherent characteristics of polyacetal resin compositions containing a polymer composition based on an olefinic polymer having glycidyl-group-containing pendent chains.

Advantageous Effect of the Invention

The resin composition of this invention based on a polyacetal resin has extremely good moldability and gives molded articles which show excellent resistance to heat aging and grease resistance with no welded sections having reduced physical properties, along with considerably improved friction characteristics. These compositions are particularly suitable as molded articles and molding materials, particularly in switching mechanism parts where wear and squeaking are critical. The addition of a dimethyl siloxane polymer considerably improves friction characteristics, and the addition of carbon black further improves moldability and wear rates. These are extremely appropriate molded articles and molding materials when used in switching mechanism parts where wear and squeaking are critical.

I claim:

1. A polyacetal composition comprising:
   a) a polyacetal resin;
   b) 2–7 parts by weight per 100 parts by weight of said polyacetal resin of a polymer composition based on an olefinic polymer having glycidyl-group containing pendant chains; and
   c) 0.5–2.5 parts by weight per 100 parts by weight of said polyacetal resin of a dimethyl siloxane polymer of a plasticity of at least one.

2. The resin composition as set forth in claim 1 in which the polymer composition comprises a single olefin type polymer having glycidyl-group-containing pendent chains.

3. The resin composition as set forth in claim 1, further comprising:
   d) styrene polymer containing oxazolyl groups;
   wherein said styrene polymer containing oxazolyl groups being present in an amount of about 50–200 parts by weight per 100 parts by weight of said olefinic polymer having glycidyl-group containing pendant chains.

4. The polyacetal resin-based resin composition as set forth in any one of claims 1 to 3, further comprising about 0.05–0.5 parts by weight of carbon black per 100 parts by weight of said resin composition.

5. A molded article obtained by molding a polyacetal resin composition as set forth in any of claims 1 to 3.

6. A molded article obtained by molding a polyacetal resin composition as set forth in claim 4.

* * * * *